United States Patent [19]

Nitsche et al.

[11] Patent Number: 5,840,905
[45] Date of Patent: Nov. 24, 1998

[54] PROCESS FOR THE PREPARATION OF 4-HYDROXY-1,2,2,6,6,-PENTAMETHYLPIPERIDINE

[75] Inventors: Karl Stephan Nitsche; Walter Wolf; Joachim Fries, all of Bensheim, Germany

[73] Assignee: Ciba Specialty Chemicals Corporation, Tarrytown, N.Y.

[21] Appl. No.: 33,450

[22] Filed: Mar. 18, 1993

Related U.S. Application Data

[63] Continuation of Ser. No. 777,492, Oct. 15, 1991, abandoned, which is a continuation of Ser. No. 451,490, Dec. 15, 1989, abandoned.

[30] Foreign Application Priority Data

Dec. 20, 1988 [CH] Switzerland .............................. 4763/88

[51] Int. Cl.⁶ .................................................. C07D 211/44
[52] U.S. Cl. ............................................. 546/184; 546/242
[58] Field of Search ..................................... 546/184, 242

[56] References Cited

U.S. PATENT DOCUMENTS

| 3,974,127 | 8/1976 | Tanikella et al. | 252/182.26 |
| 4,001,189 | 1/1977 | Tanikella et al. | 528/289 |
| 4,731,448 | 3/1988 | Issler et al. | 546/248 |
| 4,816,507 | 3/1989 | Cantatore et al. | 524/100 |
| 4,921,962 | 5/1990 | Galbo et al. | 546/184 |

FOREIGN PATENT DOCUMENTS

| 602644 | 7/1978 | Switzerland | 546/242 |

OTHER PUBLICATIONS

Helv. Chim. Acta, 49 (1), 690–695 (1966).
L. Zhelyazkov a nd N. Bikova, Farmatsiya (Sofia), 13, 11 (1963) English Translation.
Chemical Abstracts, vol. 60 (3), Abst. No. 2881–e–g Feb. 03, 1964.

*Primary Examiner*—Alan L. Rotman
*Attorney, Agent, or Firm*—Luther A. R. Hall; Michele Kovaleski

[57] ABSTRACT

A process for the preparation of 4-hydroxy-1,2,2,6,6-pentamethylpiperidine (HPMP) from 4-oxo-2,2,6,6-tetramethylpiperidine (TAA) is described, in which TAA is first reduced to 4-hydroxy-2,2,6,6-tetramethylpiperidine (HTMP) by means of catalytic hydrogenation in water, the resulting crude solution, if desired after concentration by distillation, is reacted with formaldehyde or paraformaldehyde in at least 20% molar excess, and with formic acid, and the crude product melt separated from the reaction mixture is worked up by distillation.

15 Claims, No Drawings

PROCESS FOR THE PREPARATION OF 4-HYDROXY-1,2,2,6,6,-PENTAMETHYLPIPERIDINE

This is a continuation of application Ser. No. 07/777,492, filed on Oct. 15, 1991, now abandoned, which is a continuation of application Ser. No. 07/451,490, filed on Dec. 15, 1989, now abandoned.

The present invention relates to a process for the preparation of 4-hydroxy-1,2,2,6,6-pentamethylpiperidine, hereinafter also called HPMP, by the catalytic reduction of 4-oxo-2,2,6,6-tetramethylpiperidine, also known as triacetoneamine and hereinafter abbreviated to TAA, followed by reaction of the resulting 2,2,6,6-tetramethyl-4-hydroxypiperidine (HTMP) with formaldehyde or paraformaldehyde, and subsequent working-up of the crude product by distillation.

HPMP is a useful light and heat stabilizer for plastics, but in particular is a valuable intermediate for the synthesis of a large number of light-stabilizing additives from the class of the sterically hindered piperidine compounds.

HPMP is conveniently prepared by the methylation of HTMP. A variety of methylation reactions serving this purpose are known from the literature, e.g. reaction with formaldehyde/formic acid, which is known as the Eschweiler-Clarke reaction. In this connection, see e.g. Helv. Chim. Acta 49(1), 690–695 (1966), Farmatsiya 13(3), 11–17 (1963), U.S. Pat. No. 4,001,189 (column 6) and U.S. Pat. No. 3,974,127 (column 5). The starting material used in each case is pure or commercially available HTMP. The latter is prepared from TAA by conventional reduction methods, especially by means of catalytic hydrogenation, and isolation of the final product (see e.g. Swiss patent specification 602 644). Thus it has been necessary, according to the prior art, to isolate and purify the intermediate, HTMP, in the preparation of HPMP from TAA.

The principal disadvantage of these known processes for the synthesis of HPMP is that the intermediate, HTMP, has so far always had to be isolated and/or purified, e.g. by means of salting-out or recrystallization, before being reacted further if HPMP is to be obtained in an acceptable yield. However, isolation of HTMP entails losses in yield, is time-consuming, and results in environmental pollution.

Further, U.S. Pat. No. 4,731,448 discloses a process for the preparation of another intermediate for the preparation of piperidine light stabilizers, namely 1-(2hydroxyethyl)-2,2,6,6-tetramethylpiperidine, from TAA in two steps, without isolation of the intermediate, although the second step is a completely different type of reaction, namely reaction with ethylene oxide.

It has now been found that HPMP can be obtained from TAA without the above-mentioned disadvantages, especially without isolation of HTMP, by carrying out the catalytic hydrogenation in a purely aqueous medium and reacting the resulting crude HTMP solution direct with formaldehyde and formic acid, which solution is preferably concentrated by distillation beforehand.

The present invention therefore relates to a process for the preparation of 4-hydroxy-1,2,2,6,6-pentamethylpiperidine (HPMP) from 4-oxo-2,2,6,6-tetramethylpiperidine (TAA), which process comprises reducing TAA to 4-hydroxy-2,2,6,6-tetramethylpiperidine (HTMP) by means of catalytic hydrogenation in water as solvent, reacting the resulting crude HTMP solution, as obtained or after concentration by distillation, with formaldehyde or paraformaldehyde and formic acid at 70°–150° C., without purification and/or isolation of HTMP, using formaldehyde or paraformaldehyde in at least 20% molar excess and formic acid in about stoichiometric amount, based in each case on HTMP, separating the aqueous phase of the reaction mixture from the crude product phase and working up said product phase by distillation.

The first step (catalytic hydrogenation) is carried out in water as solvent, in a manner known per se, using conventional hydrogenation catalysts, especially metal and noble metal catalysts. Especially suitable catalysts are Raney nickel and, in particular, ruthenium-on-charcoal. The hydrogenation is preferably carried out in the manner described in Swiss patent specification 602 644.

The HTMP solution obtained after hydrogenation can be further used direct, i.e. it is reacted with formaldehyde or paraformaldehyde and formic acid. It is preferred, however, to reduce the volume of the crude solution before this reaction. This is done e.g. by distillation under reduced pressure or, preferably, at normal pressure. In a preferred embodiment of the invention, at least 10%, especially at least 20%, e.g. at least 30%, of the crude HTMP solution is distilled off. Thus it is possible to distil off about 10 to 95%, e.g. 10 to 80%, preferably 10–60%, or 10–50%, for example 10–40%, or 20–50%, most preferably 20–40%, of said solution. It is also possible, however, to concentrate the crude solution until only a crude HTMP melt remains, which is then reacted direct with formaldehyde or paraformaldehyde and formic acid.

In another possible embodiment of the process of the invention, the crude HTMP solution is concentrated to an HTMP content of at least 20%, preferably at least 30% and, most preferably at least 40%. Thus, after distillation, the crude solution can have e.g. an HTMP concentration of 20–90%, preferably 30–90% and, most preferably, 40–90%, e.g. 50–90%.

Distillation of the crude HTMP solution may be carried out under normal pressure. If distillation is carried out under reduced pressure, then this pressure will conveniently be from 100 to 900, especially from 100 to 300 mbar. Depending on the chosen pressure, a two-phase mixture distils over at temperatures e.g. in the range from 30° to 100° C., especially 50° to 100° C., and is discarded.

Further reaction of the crude HTMP solution, which may or may not have been concentrated, takes place at 70°–150° C. The reaction is preferably carried out at 70°–120° C., especially at 70°–100° C., as normal pressure can be employed in the latter case. At temperatures above 100° C., the reaction is carried out in a pressure vessel (e.g. in an autoclave). If the reaction temperature is e.g. 120° C., the pressure is adjusted to about 2.5 to 3 bar. The reaction temperature is most preferably 85°–100° C.

Formaldehyde or paraformaldehyde is used in at least 20% molar excess, based on HTMP. It is convenient to use an excess of at least 40%. There is no upper limit to this excess on technical grounds; an upper limit only exists for practical economic reasons. Convenient molar excesses are normally in the range from 20 to 100%, preferably 40 to 100% and, most preferably, 40 to 70%, e.g. about 60%.

Formaldehyde is conveniently used in the form of an aqueous solution, for example as 27–50% or, preferably, as a 37% solution, i.e. formalin.

Formic acid is used in about stoichiometric amount (based on HTMP); it is self-evident that a small excess will not hinder the reaction.

When the reaction is complete, the reaction mixture is two-phase; it consists of an upper product phase (crude product phase, "crude melt") and a lower aqueous phase. For further working-up, the aqueous phase is separated from the crude HPMP melt. This is conveniently done e.g. by discharging the aqueous phase through the bottom of the reaction vessel. The crude melt is worked up by distillation. This is advantageously done by first distilling off low-boiling by-products in a conventional distillation apparatus, preferably under reduced pressure, e.g. in a vacuum of 1000–30 mbar. In particular, readily volatile fractions with a boiling point of <150° C. are removed in this step. When this distillation is complete, it is convenient, although not essential, to strip off higher-boiling by-products at about 30–10 mbar and ca. 80°–110° C., e.g. 90°–100° C. Distillation of the HPMP itself is preferably carried out at 10–2 mbar and a top temperature of 112° C.

In an alternative embodiment of the invention, an organic solvent which is sparingly miscible with water, and in which HPMP dissolves, can be added to the reaction mixture before phase separation. The HPMP then transfers into the organic phase, with which it can be separated from the aqueous phase. The organic solvent is then removed by distillation and the remaining crude HPMP melt is worked up by distillation, e.g. as described in the previous paragraph. Examples of suitable organic solvents are aliphatic, cycloaliphatic or aromatic hydrocarbons such as various petroleum ether fractions, benzene, toluene and xylene.

If desired, the HPMP distillate can then be granulated by conventional processes to give a form which has a better storage stability and is easier to handle.

Before working-up the reaction mixture, i.e. before the separation of the crude product phase or before or after addition of the organic solvent, it is convenient to destroy excess formaldehyde by the addition of a base, e.g. an organic amine or, preferably, an alkali metal or alkaline earth metal hydroxide, especially KOH or NaOH. The amount used for this purpose should be sufficient to remove the excess formaldehyde. It is preferred to add at least 30% more base than would theoretically be needed to destroy the stoichiometric excess of formaldehyde. The process of the invention can be carried out batchwise or continuously. The second step in particular can advantageously be carried out continuously by means of the apparatus conventionally used in process technology, for example a rotating disc reactor or a cascade reactor.

Conventional analytical methods can be used to determine the concentration of HTMP in the crude solution and the concentration of HPMP in the final product solution, preferably by gas chromatography.

The process of the invention makes it possible to obtain HPMP from TAA in high yields without isolation of HTMP. The process is simple to carry out, time-saving and also environmentally safe as the salt or solvent residues resulting from the salting-out or recrystallization operations hitherto employed are avoided. Another favourable consequence of the process of the invention is the higher space-time yield and lower manufacturing costs.

It is to be regarded as particularly surprising that the methylation of the HTMP effects practically 100% conversion, despite the high level of by-product resulting from not isolating the HTMP, that the reaction reaches completion in a shorter time and that even a better quality of the final product is achieved. Equally surprising is the fact that the selectivity at high temperature (e.g. 100° C.) is just as good as at a lower temperature (e.g. 70° C.).

Furthermore, the excess of formaldehyde can be kept smaller in the process of the invention than in the conventional processes. Also, the $CO_2$ formed is completely eliminated.

The following Examples illustrate the invention in more detail. Unless stated otherwise, parts and percentages are by weight in said Examples as well as throughout the entire remainder of the description and in the claims. The concentrations of HTMP and HPMP are determined in the Examples by gas chromatography.

EXAMPLE 1

1800 kg of distilled TAA (purity 92–98%) are diluted with 2200 litres of water and hydrogenated at 70° to 80° C. and under a hydrogen pressure of 10 bar in the presence of ruthenium-on-charcoal. The catalyst is then filtered off and the crude HTMP solution is stored in a tank before being processed further. Concentration of HTMP in the solution: 40%; yield: 91–97%.

EXAMPLE 2

37% of the 415 g of the crude HTMP solution obtained according to Example 1 is distilled off azeotropically at 60°–100° C. The distillate is obtained as two phases. The remaining distillation residue (216 g; HTMP content ca. 60%) is placed in a reaction vessel together with 50 g of paraformaldehyde, the mixture is heated to 86° C. and 57 g of formic acid (as an 85% aqueous solution) are then added over 20 minutes, with stirring. The reaction mixture is then heated to reflux temperature and stirred until the total reaction time is 3 hours. 85 g of 50% aqueous NaOH are then added to the reaction mixture, which is left to cool. The upper oily product phase is separated off and distilled in a conventional distillation apparatus. The readily volatile fractions with a boiling point of <150° C. are stripped off first at a top temperature of 40° C. and under a vacuum of 1000–30 mbar. The first runnings are then taken off at 30–10 mbar and a top temperature of 100° C. The main HPMP fraction is subsequently distilled over at 10–2 mbar and a top temperature of 112° C. After cooling, the product is obtained in the form of white crystals melting at 76° C. Yield after distillation: 89% of theory, based on HTMP used. Crude yield before distillation: 99–100%.

The molten product can be converted by granulation into a more advantageous form for storage. This takes place on a cooling conveyor or a cooling drum.

EXAMPLE 3

47% of the 422.6 g of the crude HTMP solution obtained according to Example 1 is distilled off azeotropically at 60°–100° C. The distillate is obtained as two phases. The remaining distillation residue (224 g; HTMP concentration ca. 70%) is placed in a reaction vessel together with 135 g of 37% formalin, the mixture is heated to 86° C. and 57 g of formic acid (as an 85% aqueous solution) are then added over 20 minutes, with stirring. The reaction mixture is then heated to reflux temperature and stirred until the total reaction time is 3 hours. 85 g of 50% aqueous NaOH are then added to the reaction mixture, which is left to cool. Further working-up is carried out exactly as described in Example 2. The yield and melting point of the HPMP are the same as in Example 2.

EXAMPLE 4

Example 3 is repeated, except that 50 g of paraformaldehyde are used instead of 135 g of formalin. HPMP is obtained in the same purity and yield as in Example 3 or 2.

EXAMPLE 5

58% of the 417 g of the crude HTMP solution prepared according to Example 1 is distilled off azeotropically at 60°–100° C. The distillate is obtained as two phases. The remaining distillation residue (175.4 g; HTMP content ca. 89%) is placed in a reaction vessel together with 42 g of paraformaldehyde, the mixture is heated to 86° C. and 57 g of formic acid (as an 85% aqueous solution) are then added over 20 minutes, with stirring. The reaction mixture is then heated to reflux temperature and stirred until the total reaction time is 3 hours. 85 g of 50% aqueous NaOH are then added to the reaction mixture, which is left to cool. Further working-up is carried out exactly as described in Example 2. The yield and melting point of the HPMP are the same as in Example 2.

EXAMPLE 6

In a mixing vessel, 100 parts of the crude HTMP solution obtained according to Example 1 are dissolved in 85 parts of 37% formalin. This mixture is heated to 80° C. and fed by means of a metering pump into a reactor, into which 36 parts of formic acid (as an 85% aqueous solution) are metered at a rate such that the temperature does not exceed 86° C. After a residence time of 2 hours, the solution is pumped through a static mixer, where it is mixed with a petroleum ether fraction (boiling range 100°–140° C.), into another stirred vessel, where the reaction solution is extracted with 30 parts of NaOH. Separation of the aqueous phase takes place in a downstream liquid/liquid separator. A further extraction with NaOH is carried out in a second extraction unit. Finally, the petroleum ether is distilled off in a distillation column and the crude melt is drawn off continuously at the bottom. The crude melt is then purified in a distillation apparatus in the manner described in Example 2. Pure HPMP is obtained in this manner in the yield and purity indicated in Example 2. Again as in Example 2, this is preferably followed by the granulation step.

What is claimed is:

1. An improved process for the preparation of 4-hydroxy-1,2,2,6,6-pentamethylpiperidine (HPMP) from 4-oxo-2,2,6,6-tetramethylpiperidine (TAA) by reducing TAA to 4-hydroxy-2,2,6,6-tetramethylpiperidine (HTMP) by means of catalytic hydrogenation, reacting the resulting crude HTMP solution, as obtained or after concentration by distillation, with formaldehyde or paraformaldehyde and formic acid at a temperature of 70°–150° C., using formaldehyde or paraformaldehyde in at least 20% molar excess, and using formic acid in about a stoichiometric amount, based in each case on HTMP, separating the aqueous phase of the reaction mixture from the crude product phase and working up the product phase by distillation, wherein the improvement comprises carrying out the entire process with water as the reaction solvent throughout and without isolating and purifying the HTMP intermediate from the catalytic hydrogenation step.

2. A process according to claim 1, wherein the crude HTMP solution is concentrated by distillation.

3. A process according to claim 2, wherein at least 10% of the crude HTMP solution is distilled off.

4. A process according to claim 2, wherein the crude HTMP solution is concentrated to an HTMP content of at least 20%.

5. A process according to claim 2, wherein the solution is concentrated to a crude HTMP melt.

6. A process according to claim 1, wherein the HTMP solution is processed further without distillation.

7. A process according to claim 1, wherein the crude HTMP solution is reacted continuously.

8. A process according to claim 1, wherein the crude HTMP solution is reacted batchwise.

9. A process according to claim 1, wherein the crude HTMP solution is reacted at a temperature of 70° to 100° C.

10. A process according to claim 1, wherein the crude HTMP solution is reacted with paraformaldehyde or 27–50% formaldehyde.

11. A process according to claim 1, wherein the molar excess of formaldehyde or paraformaldehyde is at least 40%.

12. A process according to claim 1, wherein the distilled HPMP final product is granulated after working-up by distillation.

13. A process according to claim 1, wherein an organic solvent which is sparingly miscible with water, and in which HPMP dissolves, is added to the reaction mixture before separation of the crude product phase, and this organic phase is separated from the aqueous phase.

14. A process according to claim 1, wherein excess formaldehyde in the reaction mixture is destroyed by the addition of a base before separation of the crude product phase or before or after addition of the organic solvent.

15. A process according to claim 13, wherein an aliphatic or aromatic hydrocarbon is used as the organic solvent.

* * * * *